United States Patent [19]

Hollenberg et al.

[11] Patent Number: 4,666,712

[45] Date of Patent: May 19, 1987

[54] COLD PERMANENT WAVE COMPOSITION

[75] Inventors: Detlef Hollenberg, Hilden; Hans-Wolfgang Cortekar, Langenfeld-Richrath; Karl Giede, Hilden; Horst Höffkes, Düsseldorf-Hellerhof, all of Fed. Rep. of Germany

[73] Assignee: Henkel Kommanditgesellschaft auf Aktien, Düesseldorf, Fed. Rep. of Germany

[21] Appl. No.: 817,767

[22] Filed: Jan. 8, 1986

Related U.S. Application Data

[63] Continuation of Ser. No. 679,109, Dec. 7, 1984, abandoned, which is a continuation of Ser. No. 529,544, Sep. 6, 1983, abandoned.

[30] Foreign Application Priority Data

Oct. 23, 1982 [DE] Fed. Rep. of Germany ......... 323929

[51] Int. Cl.$^4$ .............................................. A61K 7/09
[52] U.S. Cl. ........................................ 424/71; 424/72
[58] Field of Search ................ 424/70, 72, 71; 514/23

[56] References Cited

U.S. PATENT DOCUMENTS 2,982,739  5/1961  Dvorkovitz et al. ............... 252/156

FOREIGN PATENT DOCUMENTS 2421695  11/1975  Fed. Rep. of Germany .

OTHER PUBLICATIONS

Chemical Abstracts 87, 1977, p. 300, No. 172719d (Takeda).
Chemical Abstracts 93, 1980, p. 98, No. 188131r, (Empire Boeki).
European Search Report, 83110281.9.
Tradename Data Sheets (8).
Abegg et al. Chem. Abstracts, vol. 80 1974 p. 63754w.
Yotsuya et al. Chem. Abstracts, vol. 84, 1976, p. 123349n.
Kubo, et al. Chem. Abstracts vol. 92, 1980, p. 116255r.

*Primary Examiner*—Nicky Chan
*Assistant Examiner*—Jacqueline M. Stone
*Attorney, Agent, or Firm*—Ernest G. Szoke; Henry E. Millson, Jr.

[57] ABSTRACT

Hair-cosmetic compositions for improving the structure, resilience and strength of hair comprising a content of onic acids derived from aldohexoses or disaccharides containing a free aldehyde function and/or their γ- or δ-lactones and a method of improving the structure and strength of hair, particularly hair which has been adversely affected by cosmetic treatments such as dyeing, bleaching, permanent waving, etc.

2 Claims, No Drawings

COLD PERMANENT WAVE COMPOSITION

This application is a continuation of application Ser. No. 679,109, filed Dec. 7, 1984 and now abandoned, which in turn was a continuation of application Ser. No. 529,544, filed Sept. 6, 1983, now abandoned.

STATE OF THE ART

The structure of hair is damaged by regular treatment with alkaline, highly reducing or oxidizing chemicals of the type used, for example, in dyeing, bleaching or permanent waving. As a result of such structure damage, the hair suffers loss of weight, develops split ends, becomes difficult to comb and, if styled, loses its set and fullness. In addition, hair punished in this way is often dull and lifeless in appearance.

To overcome this deficiency, structure-improving agents have already been added to cosmetic preparations for hair and these structure-improving agents used are, primarily, formaldehyde and formaldehyde donors as well as S-acetyl succinic anhydride, ammonium vinyl phosphonate, ammonium phosphonate and others. It has also been proposed to use reducing sugars to improve the structure of hair and although substances such as these are effective to a certain extent, they can only be used in compositions of the type which do not react with the reducing aldehyde function. Thus, glucose cannot be used, for example, in cold-wave preparations based on thioglycolic acid or in an oxidizing media, for example bleaching preparations or developer emulsions for dyeing creams.

German Offenlegungsschrift No. 24 38 534 describes scalp-care preparations containing uronic acids, for example glucuronic acid, but, these compounds which also contain a free aldehyde function are virtually inactive as hair structurants.

OBJECTS OF THE INVENTIONS

It is an object of the invention to provide novel hair cosmetic components which improve hair structure and the ability of hair to withstand the effect of harmful chemical treatment agents.

It is another object of the invention to provide a novel method of improving the structure, resilience and strength of hair.

These and other objects and advantages of the invention will become obvious from the following detailed description.

THE INVENTION

The novel composition of the invention for improving the structure, resilience and strength of hair are hair cosmetic compositions containing an effective amount of at least one active ingredient of the group consisting of onic acids derived from aldohexoses and disaccharides containing a free aldehyde group and their $\gamma$- and $\delta$-lactones. The preferred content of said onic acids is 0.5 to 10% by weight, more preferably 1 to 5% by weight, of the hair cosmetic composition.

The structure improving effect of these onic acid additives is surprising because low molecular weight hydroxycarboxylic acids such as glycolic acid or glycerol monocarboxylic acid do not have a comparable effect and uronic acids derived from monosaccharides, for example glucuronic acid, and the sugar acids, for example mucic acid, do not have the same effect either as can be seen from Example 7.

The onic acids can be obtained from aldohexoses by careful oxidation of the aldehyde function such as with hypobromite or with dilute nitric acid. In alkaline solution, the onic acids are stable in their salt form whereas the free acids readily change into the $\gamma$- or $\delta$-lactones, the $\gamma$-lactones preferably being formed. Onic acids which likewise change readily into the corresponding $\gamma$- or $\delta$-lactones can also be obtained by careful oxidation of disaccharides containing a free aldehyde function, for example from lactose, maltose, gentobiose, cellobiose, melibiose. Gluconic acid and/or lactobionic acid are preferably used in the hair-cosmetic agents of the invention.

The hair treatment agents of the invention considerably improve the structure and strength of hair, but especially its ability to withstand damage caused by the regular application of dyes, bleaches and permanent-wave preparations. At the same time, this effect favorably influences the combability and sheen of the hair and also the set and body of hairstyles.

The hair-cosmetic agents according to the invention may be hair lotions, hair lacquers, hair sprays, dressing lotions, dressing creams, dressing gels, hair rinses, hair cures, cold-wave preparations, blow-wave preparations, toning shampoos, toning foams, dyes or permanent-wave preparations. It is particularly preferred to use the onic acids in hair-cosmetic agents containing strong reducing agents such as salts of mercaptocarboxylic acids or of sulfurous acid or strong oxidizing agents such as alkali metal bromates or hydrogen peroxide because in preparations such as these it is particularly desirable to reduce hair damage and because reducing sugars are not stable therein. Accordingly, permanent-wave preparations, permanent-wave setting solutions and developer emulsions for oxidation hair dyes containing onic acids are among the preferred embodiments of the invention.

In addition to these onic acid components, the hair treatment agents of the invention contain the usual additives for such preparations such as solvents like ethanol or isopropanol, surfactants, cosmetic oil components, polymeric film-forming agents, fragrances, dyes, complexing agents and standard hair-cosmetic active components such as revitalizing agents, cationic polymers, anti-dandruff agents, sebostatics, vitamins, antimicrobial agents and the usual substantive dyes or oxidation dye precursors for dyeing hair, the usual oxidizing agents for developing oxidation dyes, the usual reducing agents for shaping hair such as salts of thioglycolic acid or sodium sulfite or the usual oxidizing agents for setting permanent waves such as sodium bromate.

The novel method of the invention for improving the structure of human hair comprises contacting the hair with an amount of at least one active ingredient of the group consisting of onic acids derived from aldohexoses and diaccharides containing an aldehyde group and their $\gamma$ and $\delta$-lactones sufficient to improve the quality of the hair.

In the following examples there are described several preferred embodiments to illustrate the invention. However, it should be understood that the invention is not intended to be limited to the specific embodiments. The ingredients in the examples are indicated as parts by weight unless otherwise indicated.

EXAMPLE 1

A hair lotion was prepared consisting of 2 parts of Cetiol HE (a polyol fatty acid ester), 1.0 part of Extrapon Birke special, 3.0 parts of lactobionic acid, 30 parts of isopropanol, 1.0 part of perfume oil and 63.0 parts of water.

EXAMPLE 2

A hair lacquer was prepared containing 1.5 parts of Luviskol VA64 (a copolymer of vinylpyrrolidone and vinyl acetate), 1.5 parts of gluconic acid, 50.0 parts of isopropanol, 1.0 part of perfume oil and 46.0 parts of water.

EXAMPLE 3

A hair dressing cream was prepared consisting of 8.0 parts of Cetiol HE (a polyol fatty acid ester), 20 parts of isopropanol, 1.0 part of Carbopol 940, 0.8 part of triethanolamine, 4.0 parts of lactobionic acid, 1.2 parts of perfume oil and 65.0 parts of water.

EXAMPLE 4

A cold-wave emulsion was prepared consisting of 73.0 parts of water, 2.0 parts of gluconic acid, 6.0 parts of Eumulgin 384 (an emulsifier), 0.3 parts of Turpinol SL (a complexing agent), 8.0 parts of thioglycolic acid, 7.0 parts of 25% aqueous ammonium hydroxide solution, 3.0 parts of ammonium carbonate and 0.4 parts of dyes and opacifiers.

EXAMPLE 5

A cold permanent wave composition was prepared consisting of 79 0 parts of water, 2.0 parts of lactobionic acid, 3.5 parts of potassium bromate, 5.0 parts of Comperlan KD (a fatty acid alkanolamide) 10.0 parts of Texapon SG (22% sodium lauryl ether sulfate), 0.3 parts of perfume oil and 0.2 parts of dye.

EXAMPLE 6

A developer emulsion for dyeing or bleaching cream was prepared consisting of 55.2 parts of water, 0.8 parts of ammonia, 2.0 parts of gluconic acid, 2.0 parts of Texapon NSO (28% sodium lauryl ether sulfate), 2.0 parts of complexing agent, 23.0 parts of 50% hydrogen peroxide solution and 15.0 parts of Latekoll D (polymer dispersion).

EXAMPLE 7

The hair cosmetic effects of the compositions of the invention were compared with the prior art compositions in the form of an aqueous solution containing 2% by weight of the active component in deionized water. In the test, strands of hair approximately 25 cm long and weighing approximately 2 g, of the standard "light grey hair" type (Klugmann, Code 6626), were tied together at one end and accurately weighed. They were then bleached for 45 minutes at 20° C. using a standard, commercially available superbleaching cream containing 6% by weight of hydrogen peroxide and 10% by weight of $(NH_4)_2 S_2O_8$ and having a pH-value of 9.0. After rinsing with tap water at 40° C. and drying in a stream of warm air, the strands were immersed for 2 minutes in a 2% aqueous solution of the active component, for example gluconic acid. After the excess liquid had been stripped off, the strands were again dried in a stream of warm air and were then placed for 30 minutes in a standard commercially available permanent-wave emulsion containing 9.5% by weight of ammonium thioglycolate, 5% by weight of ammonium carbonate and having a pH-value of 8.8 at 20° C. and subsequently treated with a setting solution. After drying, the strands were again treated for 2 minutes with the 2% test solution and dried.

This process of bleaching, structurant treatment, permanent waving, structurant treatment was carried out three times in succession, the last structurant treatment being omitted. After drying, the strands of hair combed out under defined conditions. Because of the damage caused to the hair, combing was accompanied by a weight loss which was determined by weighing. The control value without any component treatment amounted to 45±2% by weight. The test results obtained with the ingredients of the invention and with prior art products are shown in the Table.

| 2% by weight of component in water | % Weight loss through hair damage |
| --- | --- |
| controls - no additive | 45 ± 2% by weight |
| Gluconic acid | 24 |
| Lactobionic acid | 28 |
| Glycolic acid | 42 |
| D-glucuronic acid | 43 |
| D-saccharic acid | 42 |
| Mucic acid | 44 |

The results in the Table clearly show the advantages of the compositions of the invention by their substantially reduction of weight loss while the prior art compositions had substantially no effect on weight loss.

Various modifications of the compositions and method of the invention may be made without departing from the spirit or scope thereof and it should be understood that the invention is intended to be limited only as defined in the appended claims.

What we claim is:

1. In an aqueous composition for cold permanent waving of human hair comprising an aqueous hair cosmetic composition containing at least one reducing agent selected from the group consisting of a salt of a mercaptocarboxylic acid and sulfurous acid, the improvement consisting of the addition of from 0.5 to 10% by weight of at least one second ingredient of the group consisting of (1) gluconic acid, lactobionic acid and (2) their γ- and δlactones to improve the structure, resilience and strength of human hair.

2. A composition of claim 1 containing 1 to 5% by weight of the second ingredient.

* * * * *